United States Patent [19]

Clark, Jr.

[11] Patent Number: 5,068,608
[45] Date of Patent: Nov. 26, 1991

[54] MULTIPLE COIL EDDY CURRENT PROBE SYSTEM AND METHOD FOR DETERMINING THE LENGTH OF A DISCONTINUITY

[75] Inventor: William G. Clark, Jr., Murrysville Boro, Pa.

[73] Assignee: Westinghouse Electric Corp., Pittsburgh, Pa.

[21] Appl. No.: 429,106

[22] Filed: Oct. 30, 1989

[51] Int. Cl.$^5$ ............................................. G01N 27/90
[52] U.S. Cl. ................................... 324/220; 324/232; 324/262
[58] Field of Search ............................... 324/219–221, 324/225–227, 232–234, 236–243

[56] References Cited

U.S. PATENT DOCUMENTS

| 2,992,390 | 7/1961 | De Witte | 324/220 |
| 3,241,058 | 3/1966 | Quittner | 324/242 |
| 3,675,118 | 7/1972 | Booth | 324/226 |
| 3,701,941 | 10/1972 | Bantz et al. | 324/238 |
| 3,976,936 | 8/1976 | Nishino | 324/232 |
| 4,016,487 | 4/1977 | Neumaier | 324/232 |
| 4,101,832 | 7/1978 | Baker et al. | 324/227 |
| 4,234,848 | 11/1980 | Diem et al. | 324/262 |
| 4,258,319 | 3/1981 | Shimada et al. | 324/242 X |
| 4,288,747 | 9/1981 | Kawabata et al. | 324/243 X |
| 4,325,026 | 4/1982 | Cooper, Jr. et al. | 324/232 |
| 4,651,093 | 3/1987 | Detriche et al. | 324/232 |
| 4,739,261 | 4/1988 | Sugiyama et al. | 324/232 |
| 4,855,677 | 8/1989 | Clark, Jr. et al. | 324/220 X |
| 4,860,756 | 8/1989 | Ko et al. | 324/232 X |

FOREIGN PATENT DOCUMENTS

| 55-48649 | 7/1980 | Japan . |
| 56-154657 | 1/1981 | Japan . |
| 0017353 | 2/1983 | Japan | 324/232 |
| 252631 | 2/1970 | U.S.S.R. . |
| 673904 | 7/1979 | U.S.S.R. . |
| 1298633 | 3/1987 | U.S.S.R. . |

OTHER PUBLICATIONS

"LAB KIT for Magnetic Shielding with AC Magnetic Pick Up Probe", Brochure Magnetic Shield Division, Perfection Mica Company, 1983.

*Primary Examiner*—Gerard R. Strecker

[57] ABSTRACT

Both a system and a method for determining the length of a discontinuity such as a crack or other fault in the interior wall of a steam generator heat exchanger tube is disclosed herein. The apparatus generally comprises an elongated probe assembly which includes a plurality of eddy current coils mutually separated at known distances with respect to each other along the longitudinal axis of the probe, and an eddy current coil actuating device for separately and independently actuating each of the coils to provide an adjustable electromagnetic sensing field. In the method of the invention, the probe assembly is positioned adjacent a discontinuity and then each eddy current coil, separated by a known distance, is independently actuated and its reading recorded to determine which of the coils actually detects the discontinuity. The length of the discontinuity may then be generally inferred from the known distances that separate the eddy current coils that detect the extremities of the crack or other discontinuity. A more specific sizing of the length of the crack is then obtained by actuating the eddy current coils that are located just outside the extremity-detecting coils at progressively lower frequencies until field of these outside coils finally couples with the extremities of the crack.

19 Claims, 2 Drawing Sheets

MULTIPLE COIL EDDY CURRENT PROBE SYSTEM AND METHOD FOR DETERMINING THE LENGTH OF A DISCONTINUITY

BACKGROUND OF THE INVENTION

This invention generally relates to a system and method for determining the length of a discontinuity in an electrically conductive object using a probe which includes a plurality of eddy current coils which may be actuated independently. The system is specifically concerned with inspecting the interiors of the heat exchanger tubes of nuclear steam generators.

Systems for inspecting metallic objects for defects are well known in the art, particularly for tube wall inspection. Such systems typically employ a probe having one or more eddy current coils to detect the presence or absence of discontinuities in the tube wall created by cracks or pits. Generally, an alternating current is conducted through the coil or coils to emanate a time-varying magnetic field which in turn induces eddy currents in the inner walls of the tube as the coil is moved axially. Because the eddy currents create a magnetic field which is opposite in polarity to the time-varying magnetic field emanated by the probe coil, the eddy currents generated in the tube apply a measurable impedance to the alternating current that fluctuates through the coil. This impedance is highest when the metal conducting the eddy current is free from discontinuities such as cracks or pits or other imperfections of the metal.

Prior art eddy current probes typically have one or two coils which are moved along the longitudinal axis of the heat exchanger tube being inspected by a cable-pusher mechanism. When the eddy current coils come in the vicinity of a crack or a pit, or other discontinuity in the metal wall of the tube, the system operator takes note of the axial position of the probe at the time when the electromagnetic field emanated by the probe beings to interact with the discontinuity, as well as the point at which such interaction ceases. Because the system operator knows how many centimeters of flexible cable have been extended upwardly through the open end of the tube at the time when the flow is first detected and last detected by the eddy current probe coils, the axial position of the flaw along the longitudinal axis of the tube may be determined. Unfortunately, the drive cable used to axially extend and withdraw the probe along the interior of the tube has some amount of tensile and compressive yieldability, which in turn introduces inaccuracies in the axial measurements of the location of flaws along the longitudinal axis of the tube. Moreover, while such probes have proven themselves capable of generally locating the position of the flaw along the longitudinal axis of such tubes, the relatively rapid axial movement of the probe, in combination with the aforementioned tensile and compressive properties of the pusher cable, makes it particularly difficult for the system operator to accurately locate the extremities of the crack or other flaw. This is a significant limitation, as the axial length of such cracks or other flaws is an important factor in determining both the overall condition of the heat exchanger tube, as well as the appropriate maintenance operation (which may involve either sleeving the tube, or plugging it in cases of severe degradation).

Of course, a slower axial movement of the probe through the tube can enhance the accuracy of the system in determining the precise locations of the flaw extremities. A more positive driving mechanism, such as a lead screw, may also be used to both axially and rotatably sweep the probe around the interior of the tube walls in a helical fashion to obtain more detailed information concerning the location of the flaw extremities, as well as the orientation of the flaws. Such a lead screw driving mechanism has been used in conjunction with the pancake-type eddy current coil probes developed and patented by the Westinghouse Electric Corporation. However, while the slower and more precise driving of eddy current probes through such heat exchanger tubes does result in enhanced flaw detection accuracy, it does so at the expense of increased inspection times. This is a significant limitation, as such nuclear steam generators typically have over 40 miles of tubing, and as every day of down time caused by such tube inspections typically caused the electric utility over $500,000.00 a day in lost revenues.

Clearly, there is a need for a system and method for rapidly and accurately detecting the lengths of cracks and other discontinuities in the heat exchanger tubes of nuclear steam generators to determine the axial extent of damage that may exist therein so that the most appropriate maintenance procedures may be correctly chosen. Ideally, such an inspection system should allow determination of the length of a defect located in a tube without requiring the pushing and pulling of long drive cables which can axially stretch or compress, thereby limiting the accuracy of the measurement due to slack or "wind-up", or the use of relatively show helical drive mechanisms which provide the desired accuracy at the expense of increased operating time.

SUMMARY OF THE INVENTION

Generally, the invention is both a system and a method for determining the length of a discontinuity in an electrically conductive object, such as the interior wall of a steam generator heat exchanger tube, which coordinates the operation of a plurality of axially spaced eddy current probes to measure the length of a discontinuity. The apparatus generally comprises an elongated probe assembly which includes a plurality of eddy current coils mutually separated at known distances with respect to each other along the longitudinal axis of the probe and an eddy current coil actuating device for separately and independently actuating each of the coils to provide in electromagnetic sensing field of adjustable length. Further, magnetic field insulator are provided between each of the coils to eliminate cross-talk. Preferably, the eddy current coils are arranged in tandem with their axis of rotation being mutually collinear in a stacked array to allow efficient tube wall scanning. Because each coil may be separately and independently actuated by, for example, the combination of a multi-frequency current generator and a computer control, two of the centrally located eddy current coils may be used as a dual element differential probe for initially locating the discontinuity prior to measuring its axial length. Moreover, the computer control may be used to actuate each coil at alternating currents of different frequencies at different times so that each individual coil is capable of emanating electromagnetic fields of different sizes.

In operation, the probe assembly is first inserted into the open end of a tube to be inspected. Next, two adjacent eddy current probes located in the middle of the probe array are actuated to detect the presence of a crack or other flaw in the tube. During this step, the operator moves the probe assembly so the signal from the two centrally located probes is maximized, which results in the central portion of the probe assembly being positioned directly adjacent to the crack or other flaw. Next, each eddy current coil is independently actuated and its readings recorded to determined which of the eddy current coils is located at the extremities of the discontinuity. Since the distances between the coils are known, the operator can generally infer the length of the crack or other flaw from this information. The extremities of the discontinuity are then determined with greater accuracy by actuating the coils located immediately outside of the coils which detected the extremities of the crack at a plurality of frequencies that are progressively lower until these outer coils detect the outer ends of the crack. The axial length of the crack can then be accurately inferred from the known discontinuity detecting range associated with the frequency of the current conducted through the outer coils.

The system and method are capable of quickly and accurately locating and measuring the length between the extremities of a crack or other discontinuity without depending on the flexible drive cables or lead screw drive mechanisms used in the prior art.

BRIEF DESCRIPTION OF THE SEVERAL FIGURES

DETAILED DESCRIPTION OF THE PREFERRED EMBODIMENT

Figure 1:
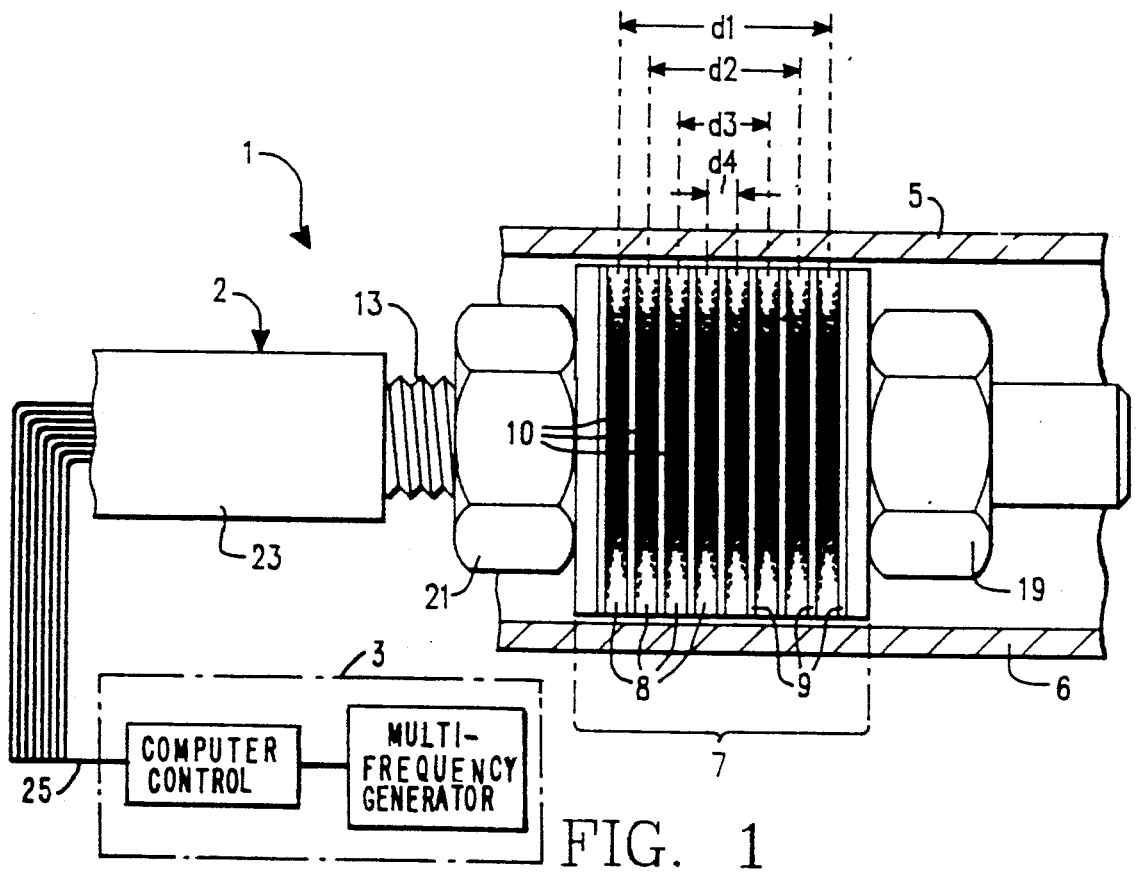
FIG. 1 is a side view of the system of the invention as it would appear prior to inspection of a discontinuity in a heat exchanger tube in a nuclear steam generator.
Figure 2:
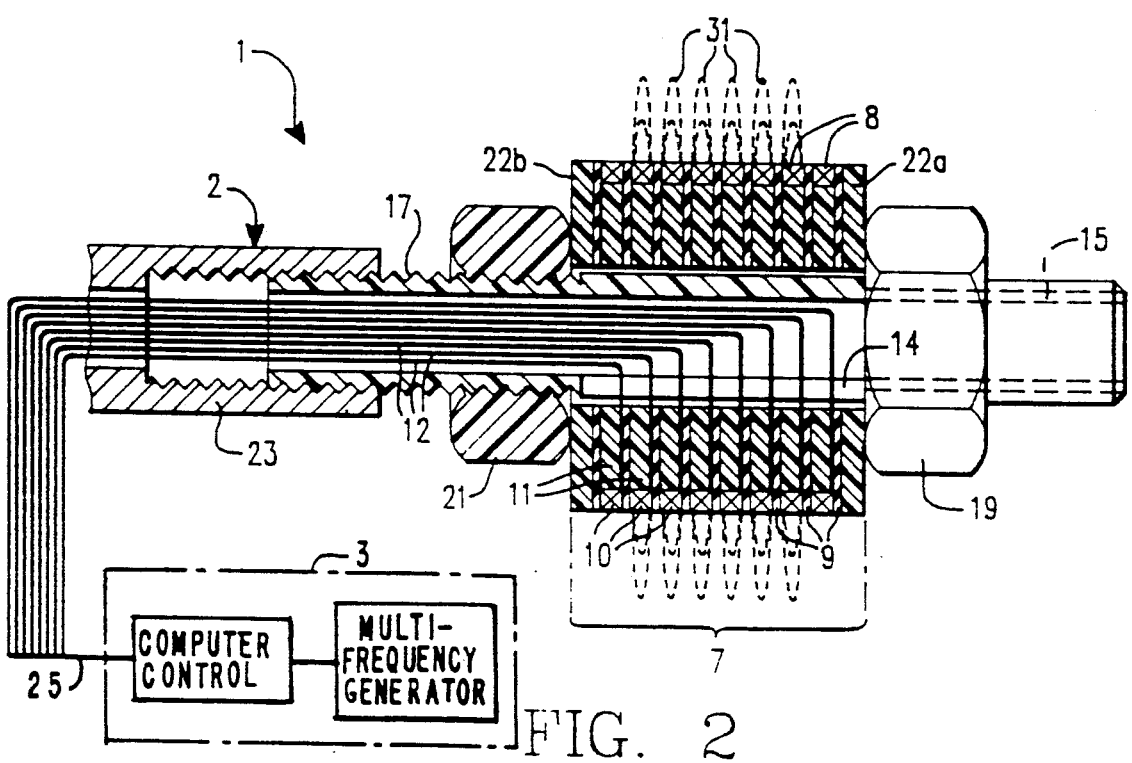
FIG. 2 is a cross-sectional side view of the ruler probe used in the inspection system of the invention.

With reference now to FIGS. 1 and 2, wherein like numerals designate like components throughout all the several figures, this system 1 for detecting the length of a discontinuity in an electrically conductive object generally comprises a probe assembly 2 which is electrically connected to the combination of a multiple frequency current generator and a computer control 3. In the preferred embodiment, the multiple frequency current generator used is a MIZ 18 Model multifrequency generator manufactured by Zetec located in Isaquah, WA, and the computer control is a Hewlett Packard Type HP 9836A containing a Motorola MC 6800 microprocessor. The system 1 is particularly useful in detecting the length of a crack or other discontinuity in the wall 5 of a heat exchanger tube 6 located in the steam generator of a nuclear or conventional steam generator.

The probe assembly 2 generally comprises a stack 7 of ring-shaped bobbin coils 8 which are separated from one another by magnetic insulators 9. In the preferred embodiment, the magnetic insulators 9 are ring-shaped laminates of netic-conetic material of the type described in U.S. Pat. application Ser. No. 167,289 filed Mar. 3, 1988 and entitled "Multiple Coil Eddy Current Probe and Method of Flaw Detection", assigned to the Westinghouse Electric Corporation. Each of the bobbin coils 8 is formed from a coil 10 of copper wire which is wound about a support ring 11 formed from nylon or Delrin ® or some other easily fabricated, plastic material. In the preferred embodiment, each of the coils 10 is formed from 64 turns of 36 gauge copper wire. Each of these coils 10 terminates in a pair of lead wires 12 as is best seen in FIG. 2.

Each of the bobbin coils 8 is stacked in tandem onto a probe support tube 13 such that the axes of rotation of each of the ring-shaped coils 10 thereon are collinear. The probe support tube 13 includes a slot for conducting the lead wires 13 of each of the bobbin coils 8 through its hollow interior. The probe support tube 13 further includes distal and proximal threads 15 and 17 for accommodating distal and proximal mounting nuts 19 and 21 which serve to hold the stack 7 of bobbin coils 8 together. In the preferred embodiment, both the probe support tube 13 and the mounting nuts 19 and 21 are all formed of either nylon, Delrin ®, or some other plastic material which is not electrically conductive. It should be noted that nylon, washer-shaped spacers 22a,b are located at either ends of the stack 7 of bobbin coils 8, and serve to protect the delicate windings of the leading and trailing bobbin coils 8 during the operation of the system 1.

As is best seen in FIG. 2, the lead wires 12 of each of the bobbin coils 8 all pass through the slot 14 in the probe support tube 13 and are conducted through the hollow interior of the tube 13 and gather together within a connector assembly 23 located at the proximal end of the probe assembly 2. Although not expressly shown in FIG. 2, these lead wires are all connected to a multiple-conductor cable 25 which is in turn plugged into the input of the computer controlled multiple frequency generator 3.

The number of coils 8 within the coil stack 7 determines the degree of accuracy of the probe assembly 2 in determining the length of a crack or other flaw in the walls 5 of a heat exchanger tube 6. In the preferred embodiment, the axial length of the coil stack 7 is approximately 1.76 cm., which yields inaccuracy of approximately two mm. The axial length of the coil stack 7 will depend upon minimum length of a crack or other fault in a tube that is unacceptable for a given tubing application. For example, if it has been established that axial damage in excess of 1 cm. is unacceptable for a given tubing application, the provision of a stack 7 of bobbin coils 8 much longer than about 0.8 cm. would not be necessary.

As is shown in FIG. 1, the distances between the various bobbin coils 8 in the stack 7 are known. For example, the distance between the two outer most coils 8 is d1, while the distance between the two adjacent, innermost coils is only d4. As will be seen shortly, the known distances d1, d2, d3 and d4 between various pairs of the bobbin coils 8 in the stack 7 allows the system operator to determine the approximate axial length of any crack or other flaw in the tube walls 5 in a rapid and effective manner. As is evident in FIG. 2, each of the coils 8 is capable of generating its own independent magnetic field 31. The netic-conetic material used in the magnetic insulators 9 prevent significant cross-talk from occurring between the adjacent fields 31 generated by adjacent bobbin coils 8. While FIG. 2 illustrates the magnetic fields that would be generated if the six central bobbin coils 8 were simultaneously actuated, it should be noted that each of the pairs of lead wires 12 of each of the bobbin coils 8 are separately connected to the computer controlled, multi-frequency generator 3, and that the multi-frequency generator 3 is capable of actuating any one or all or any combinations of the bobbin coils 8 in accordance with the wishes of the system operator.

Figure 3A:
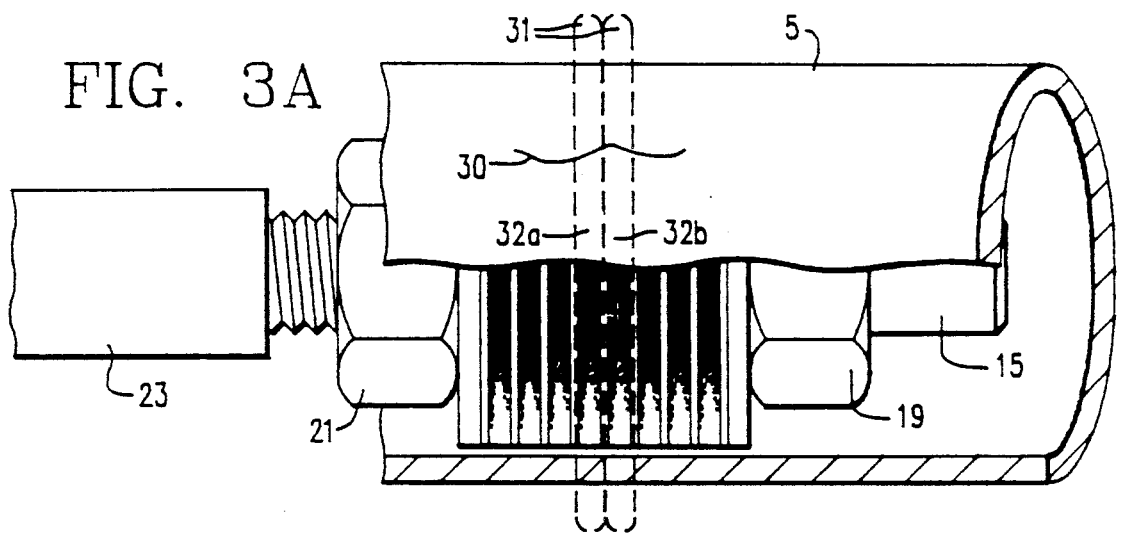
FIGS. 3A-3C are side views of the ruler probe illustrating how the ruler probe is used in implementing the method of the invention.
Figure 3B:
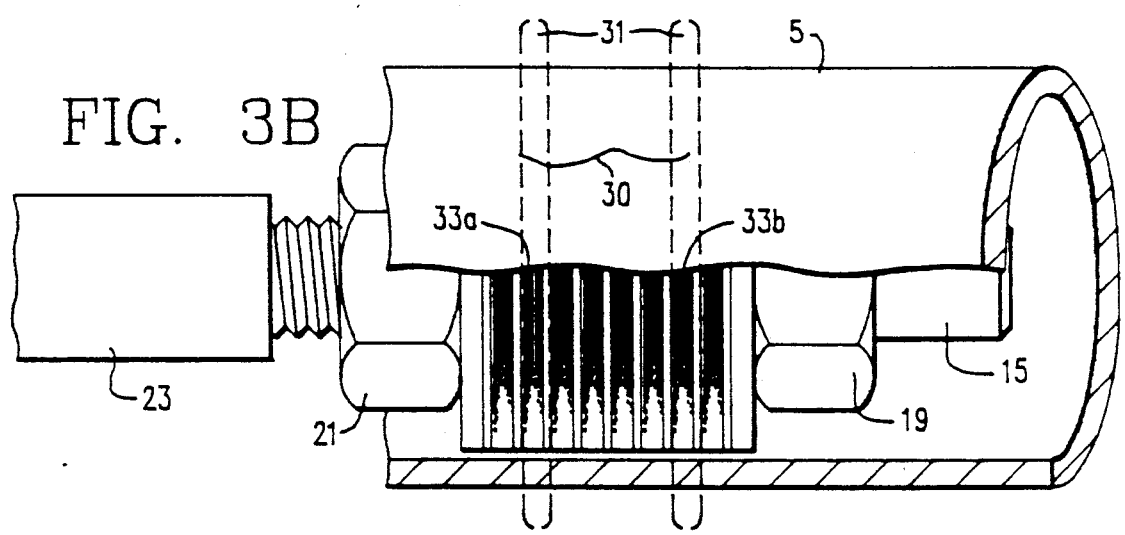
Figure 3C:
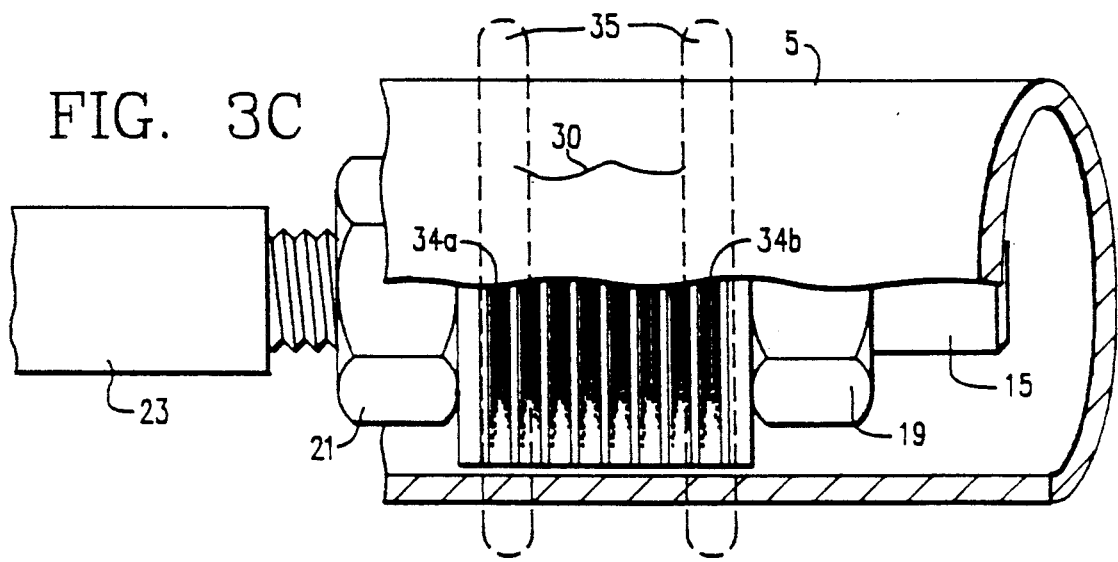

The method of the invention is best understood with reference to FIGS. 3A, 3B and 3C. In the first step of this method (which is illustrated by FIG. 3A), the two central most bobbin coils 32a,b of the coil stack 7 are actuated and are operated in exactly the same manner as a differential eddy current probe in order to initially locate a discontinuity such as an axial crack 30 in the wall 5 of a heat exchanger tube 6. An initial detection frequency of 100 to 400 HZ has been found to be an appropriate range. During this step of the method of the invention, the system operator manipulates the probe assembly 2 by means of a flexible cable which serves to either push or pull the probe assembly 2 to a desired location along the axis of the heat exchanger tube 6. When the system operator initially detects the presence of a flaw such as the axial crack 30, he then carefully manipulates the probe assembly 2 while monitoring the impedance generated in the multi-frequency current generator 3 in order to place the centrally located coils 32a,b as close as possible to the axial center of the crack 30.

Once the probe assembly 2 has been placed into the position illustrated in FIG. 3A, the system operator begins to independently actuate bobbin coils 33a,b which are located outside of the centrally located bobbin coils 32a,b in order to locate the position of the extremities of the crack 30. All during this step, the probe assembly 2, of course, remains stationary. Additionally, the system operator chooses a current frequency which generates a magnetic field which does not expand out of the axial confines of the bobbin coils 33a,b emanating the field. The initial extremity frequency range may be between 500 KHZ and 1 MHZ.

Finally, the precise location of the axial extremities of the crack 30 are located by actuating the bobbin coils 34a,b which are immediately outside of the extremity-detecting coils 33a,b, and conducting progressively lower frequency alternating current through them. An appropriate lower frequency sweep may be between 50 and 200 KHZ. The effect of conducting such lower-frequency alternating currents through this outside coils 34a,b is to create magnetic fields 35 which are axially larger than the magnetic fields 31 generated by the higher-frequency alternating currents. The system operator carefully monitors the frequencies of the currents conducted through these outer coils 34a,b which first results in the detection of the outer most extremities of the crack 30. Because the system operators knows the precise distances that the extremity detecting coil 33a,b and 34a,b are with respect to one another, and further, because the system operator knows the precise extent to which the magnetic fields 35 generated by the coils 34a,b expand with every incremental decrease in the frequency of the current conducted through them, the system operator can now accurately and confidently compute the axial length of the crack 30.

Thus, the precise distances between the extremities of the crack 30 are determined by a stationary probe assembly 2 which is capable of varying the axial length of the electro-magnetic field generated by its component bobbin coils 8. The system 1 of the invention is capable of accuracies far greater than that of conventional eddy current probe coils, which are moved by drive system characterized by unwanted axial slack.

I claim:

1. A system for determining the length of a discontinuity in an electrically conductive object, comprising an elongated probe assembly including a linear array of eddy current coils mutually separated at known distances with respect to each other along the longitudinal axis of the probe and an eddy current coil actuating means for separately, independently and sequentially conducting alternating current of a first frequency through said eddy current coils in said array and then for conducting alternating current of a second frequency through at least two of said coils to incrementally adjust the length of the electromagnetic sensing field along the longitudinal axis of said probe such that the length of a discontinuity located between eddy current coils in said linear array of coils is determined without the need for moving the probe assembly.

2. A system for determining the length of a discontinuity as defined in claim 1, further comprising magnetic field insulators for eliminating cross-talk between the eddy current coils 3. A system for determining the length of a discontinuity as defined in claim 1, wherein said eddy current coils are arranged in tandem with their axis of rotation being mutually collinear.

4. A system for determining the length of a discontinuity as defined in claim 2, wherein said eddy current coils are arranged in a stacked array in said probe assembly.

5. A system for determining the length of a discontinuity as defined in claim 4, wherein one of said magnetic field insulators is disposed between each of said eddy current coils.

6. A system for determining the length of a discontinuity as defined in claim 5, wherein each of said magnetic field insulators includes netic-conetic shielding.

7. A system for determining the length of a discontinuity as defined in claim 1 wherein said electrically conductive object is a metallic tube.

8. A system for determining the length of a discontinuity as defined in claim 1 wherein said eddy current coil actuating means includes a computer control.

9. A system for determining the length of a discontinuity as defined in claim 8 wherein said computer control may energize at least two of said plurality of eddy current coils as a dual element differential eddy current probe to sense the presence of a discontinuity.

10. A system for determining the length of a discontinuity as defined in claim 9 wherein said computer control operates said eddy current coil actuating means to provide alternating current of different frequencies through said eddy current coils at different times.

11. A system for determining the length of discontinuity as defined in claim 8 wherein said computer control varies the frequency of alternating current conducted through each eddy current coil to create a variable sized electromagnetic field along the longitudinal axis of said probe assembly.

12. A system for determining the length of a discontinuity as defined in claim 1 wherein said eddy current coil actuating means includes a generator means capable of generating alternating current at a selected frequency.

13. A system for determining the length of a discontinuity as defined in claim 12 wherein said probe assembly includes at least four equally spaced eddy current coils per centimeter of axial probe length.

14. A method for determining the length of a discontinuity in an electrically conductive object by means of an elongated probe assembly which includes a linear array of eddy current coils mutually separated by a known distance along the longitudinal axis of said probe assembly and means for separately and independently actuating each of said coils, comprising the steps of:

positioning the probe assembly adjacent to a discontinuity, and independently actuating said eddy current coils by sequentially conducting an alternating current of a first frequency through said eddy current coils in said array and recording which of said eddy current coils detects said discontinuity to infer the length of said discontinuity form the known distances that separate the eddy current coils that detected the extremities of the discontinuity, and conducting alternating current of a second frequency through at least some of said coils to more precisely determine the length of the discontinuity.

15. A method for determining the length of a discontinuity as defined in claim 14, wherein at least one eddy current coil that is centrally located on the longitudinal axis of the probe assembly is used to sense the presence of a discontinuity in the metallic object and to position the probe assembly adjacent to a discontinuity.

16. A method for determining the length of a discontinuity as defined in claim 15, wherein two eddy current coils centrally located on the longitudinal axis of the probe assembly are operated as a differential eddy current sensor to position a central portion of the probe assembly adjacent to a discontinuity.

17. A method for determining the length of a discontinuity as defined in claim 14, wherein during the third step of said method wherein the length of said discontinuity is inferred the eddy current coils located immediately beyond the eddy current coils that detected the extremities of the discontinuity are actuated by conducting an alternating current therethrough at a plurality of frequencies that are progressively lower than said first frequencies, wherein each of said progressively lower frequencies extends the discontinuity range of said eddy current coils by a known length, until said low frequency conducting coils detect said discontinuity, and wherein the position of the extremities of the discontinuity between the outermost discontinuity detecting coils and the low frequency conducting coils is accurately inferred form the known discontinuity detecting range associated with the frequency that resulted in detection of said discontinuity.

18. A method for determining the length of a discontinuity in an electrically conductive object by means of an elongated probe assembly which includes a plurality of eddy current coils mutually separated by a known distance along the longitudinal axis of said probe assembly and means for separately and independently actuating each of said coils, comprising the steps of:

actuating at least one of said eddy current coils of said probe assembly to determine the position of a discontinuity and positioning a central portion of said probe assembly adjacent to said discontinuity;

actuating independently each of said plurality of eddy current coils in a controlled sequence to determine which coils detect said discontinuity;

estimating a first discontinuity length from the known distance between the eddy current coils that detect the extremities of said discontinuity;

sizing said discontinuity length by actuating at progressively lower frequencies eddy current coils that are located immediately beyond said extremities detected until the extremities of said discontinuity are detected by said low frequency conducting coils, and determining the length of said discontinuity from the known eddy current coil distances along said probe assembly and from the known extension in the range of discontinuity detection afforded by the lower frequency that resulted in detection of the discontinuity extremities by the low frequency conducting coils.

19. A system for determining the length of a discontinuity in a tube, comprising an elongated probe assembly including a stacked, linear array of eddy current coils separated by known distances along the longitudinal axis of said probe assembly, wherein the axes of rotation of the coils are mutually colinear, and magnetic shield insulators between adjacent coils to prevent cross-talk therebetween, and an eddy current coil actuating means for separately, independently and sequentially conducting alternating current through said coils in said array to incrementally adjust the length of the electromagnetic sensing field along the longitudinal axis of said probe such that the length of discontinuity located between coils is determined by the known distances between the coils without the need for moving the probe assembly with respect to the discontinuity.

* * * * *